(12) United States Patent
Guo et al.

(10) Patent No.: US 8,044,063 B2
(45) Date of Patent: Oct. 25, 2011

(54) QUINAZOLINE DERIVATIVES USEFUL AS ANTI-TUMOR MEDICAMENT

(75) Inventors: Jianhui Guo, Shanghai (CN); Meng Wang, Shanghai (CN); Yong Jiang, Shanghai (CN); Xiaofang Zhang, Shanghai (CN)

(73) Assignee: Shanghai Allist Pharmaceuticals, Inc., Shanghai (CN)

( * ) Notice: Subject to any disclaimer, the term of this patent is extended or adjusted under 35 U.S.C. 154(b) by 104 days.

(21) Appl. No.: 12/096,508

(22) PCT Filed: Oct. 20, 2006

(86) PCT No.: PCT/CN2006/002786
§ 371 (c)(1),
(2), (4) Date: Jul. 23, 2008

(87) PCT Pub. No.: WO2007/082434
PCT Pub. Date: Jul. 26, 2007

(65) Prior Publication Data
US 2008/0300248 A1    Dec. 4, 2008

(30) Foreign Application Priority Data
Jan. 20, 2006   (CN) .......................... 2006 1 0023526

(51) Int. Cl.
*A61K 31/517* (2006.01)
(52) U.S. Cl. ..................... 514/266.4; 544/283
(58) Field of Classification Search ............... 514/266.4; 544/283
See application file for complete search history.

(56) References Cited

FOREIGN PATENT DOCUMENTS

| CN | 1100046 C | 1/2003 |
|---|---|---|
| EP | 0 520 722 A1 | 12/1992 |
| EP | 0 566 226 A1 | 10/1993 |
| EP | 0 635 498 A1 | 1/1995 |
| WO | WO 96/09294 | 3/1996 |
| WO | WO 96/15118 | 5/1996 |
| WO | WO 96/30347 | 10/1996 |
| WO | WO 96/33980 | 10/1996 |
| WO | WO 97/30034 | 8/1997 |
| WO | WO 97/38983 | 10/1997 |
| WO | WO 99/06378 | 2/1999 |
| WO | WO 99/35146 | 7/1999 |
| WO | WO 00/06555 | 2/2000 |
| WO | WO 01/04111 A1 | 1/2001 |
| WO | WO 01/21594 A1 | 3/2001 |
| WO | WO 01/21596 A1 | 3/2001 |
| WO | WO 01/32155 A2 | 5/2001 |
| WO | WO 2005/046678 | * 5/2005 |
| WO | WO 2005/040125 A1 | 5/2005 |
| WO | WO 2006/071017 | * 7/2006 |
| WO | WO 2006/090717 | * 8/2006 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Blackledge G. et al., "Anti-EGF Receptor Therapy", *Prostate Cancer and Prostatic Diseases* 3(4):296-302 (2000).
Baselga J. et al., "ZD1839 ('Iressa')[1,2] as an Anticancer Agent", *Drugs 60, suppl.* 1:33-40 (2000).
Denny W.A., "The 4-Anilinoquinazoline Class of Inhibitors of the *erbB* Family of Receptor Tyrosine Kinases", *IL Farmaco* 56:51-56 (2001).
Brignola P.S. et al., "Comparison of the Biochemical and Kinetic Properties of the Type 1 Receptor Tyrosine Kinase Intracellular Domains", *The Journal of Biological Chemistry* 277(2):1576-1585 (2002), XP-002531671.

* cited by examiner

*Primary Examiner* — James O Wilson
*Assistant Examiner* — Douglas M Willis
(74) *Attorney, Agent, or Firm* — Scully, Scott, Murphy & Presser, P.C.

(57) ABSTRACT

The present invention relates to quinazoline derivatives of the formula (I) useful as anti-tumor medicaments, or a pharmaceutically acceptable salt thereof, the definition of the substituents $R_1$, $R_1'$, $R_2$, $R_2'$ are as defined in the description. It also relates to a pharmaceutical composition containing same, and a method for the preparation of quinazoline derivatives of formula (I) or a pharmaceutically acceptable salt thereof.

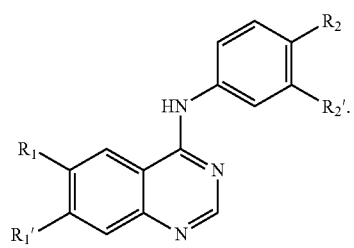

4 Claims, 1 Drawing Sheet

QUINAZOLINE DERIVATIVES USEFUL AS ANTI-TUMOR MEDICAMENT

FIELD OF THE INVENTION

The present invention relates to compounds usable as irreversible inhibitors of tyrosine kinase, especially to quinazoline derivatives. The invention also relates to the method for preparing the compounds, and to a pharmaceutical composition comprising the said quinazoline derivatives.

BACKGROUND OF THE INVENTION

Cancer is regarded as a disease in the intracellular signal transduction system or in the mechanism of the signal transduction. The cell accepts many extracellular orders and decides whether or not to proliferate. The aim of the signal transduction system is to accept these or other signals from the cell surface, and to transfer them into cells. And then these signals are conducted to cell nucleus, cytoskeleton and the structure for transportation and protein synthesis.

The most common pathogenesis for cancer is a series of defects. The mentioned defects can be that of some proteins (when mutation occurs) or the defects in the regulation of the amount of the intracellular protein, which result in excessive or deficient production of the proteins. Generally, the constitutive state can be induced by a significant trauma in a cell, and a signal for proliferation is thus received by the cell nucleus, while this signal is inexistent in fact. The above mentioned procedure can be mediated by many kinds of mechanisms. Sometimes, some cells will start producing true growth factors for their own receptors in unnecessary cases, which is so-called autocrine loop mechanism.

There are many receptors on the cell surface. The interaction between the growth factors and these receptors is essential for the regulation of normal cellular growth. However, in some cases, the overexpression or mutation of the abnormal receptors will result in uncontrollable proliferation, which may induce tumor growth and cancer at last.

Epidermal cell growth factors receptors (EGFR) are identified as one significant driving factor in the process for cellular growth and proliferation. In common cancer, such as non-small cell lung cancer, the epidermal cell growth factors receptors are expressed excessively far above the normal level. The epidermal cell growth factors receptors family is composed of EGFR (Erb-B1), Erb-B2 (HER-2/neu), Erb-B3 and Erb-B4. The epidermal cell growth factors receptors are concerned in the process for most cancer, especially colon cancer and breast cancer. The overexpression and mutation of the receptors have been proved to be the leading risk factor for a bad-prognosis breast cancer. Besides, it has been verified that each of the above four members of the receptors family can aggregate with another member into a heterodimer, and form a signal delivery complex. Overexpression of more than one member of this family in a malignant tumor will result in a synergistic signal delivery.

EGFR belongs to the protein tyrosine kinase (PTK) family. The protein tyrosine kinase is an enzyme which catalyzes the transportation of phosphate groups from ATP to the tyrosine residue located in a protein substrate. Protein tyrosine kinases play important roles in normal cell growth. The overexpression of EGFR may cause the activation of receptors without ligands, and the phosphorylation of some proteins, and then the signal for cell division is produced. As a result, EGFR may magnify the weak signal excessively by the auto-tyrosine-kinase action, and render the overproliferation of cells.

Due to the importantance of the abnormal receptor kinases in the mechanism for the onset of cancer, many researches have been involved in searching for specific PTK inhibitors as potential anti-cancer drugs recently. European patent application 520722A1 discloses certain 4-phenylamino-phthalazinone derivatives with inhibitory activity against PTK. European patent application 566226A1 discloses some 4-phenylamino-phthalazinone derivatives with substituents at position 5 to position 8 having PTK inhibitory activity. European patent application 635498A1 discloses that certain 4-phenylamino-phthalazinone derivatives with various substituents at position 6 and with a halogen at position 7 also possess PTK inhibitory activity.

The international publication WO96/30347 (Chinese patent CN96102992) relates to a series of 4-(substituted-phenylamino)-quinazoline derivatives, the prodrugs and the pharmaceutical acceptable salts thereof, which are used in treating diseases induced by overproliferation.

The international publication WO97/38983 (Chinese patent CN97194458) provides the compounds useful as irreversible inhibitors against tyrosine kinase.

The international publication WO 00/06555 (Chinese patent CN99808949) also relates to certain substituted quinazoline compounds that possess PTK inhibitory activity.

The international publication WO 99/35146 (Chinese patent CN99803887) discloses bicycloheteroaromatics as inhibitors against protein tyrosine kinase.

However, there remains the need in this field for new inhibitors effective against protein tyrosine kinases.

SUMMARY OF THE INVENTION

The present invention provides a compound of formula I, or a pharmaceutically acceptable salt, or a solvate thereof,

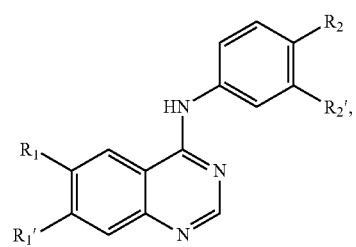

wherein, $R_1$ is selected from;

(a) Halogen, $C_1$-$C_4$alkyl, $C_1$-$C_4$alkyl substituted by halogens, $C_1$-$C_4$alkoxy, $C_1$-$C_4$alkoxy substituted by halogens, methoxyethoxy, N-morpholinopropoxy, ester group, acylamino or sulfonamide group;

(b) Unsubstituted or substituted phenyl, wherein the substituents are 1-3 substituents selected from the group consisting of halogen, —OH, $C_1$-$C_4$alkyl, $C_1$-$C_4$alkoxy, $C_1$-$C_4$alkyl-OH, $C_1$-$C_4$alkoxymethyl, $C_2$-$C_4$ester group, or sulfonate;

(c) Unsubstituted or substituted furyl, Unsubstituted or substituted thienyl, wherein the substituents are 1-3 substituents selected from the group consisting of halogen, —OH, —$NH_2$, $C_1$-$C_4$alkyl, $C_1$-$C_4$alkoxy, alkoxymethyl, ester group, or sulfonate; or $R_1$ is

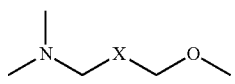

Wherein R₁ is attached to the ring via oxygen, and X is selected from furyl, pyrrolidyl, pyridyl, oxazoline, thiazolyl, or thienyl;

$R_1'$ is selected from hydrogen, $C_1$-$C_4$alkyl, $C_1$-$C_4$alkyl substituted by halogens, $C_1$-$C_4$alkoxy, or $C_1$-$C_4$alkoxy substituted by halogens;

$R_2$ is selected from benzyl, mono-, di- or tri-halobenzyl, benzoyl, pyridylmethyl, pyridylmethoxy, benzyloxy mono-, di- or tri-halobenzyloxy or mono-, di- or tri-halophenylsulfonyl, furylmethyl, pyrrolylmethyl, pyrrolylmethoxy, halogen, $C_1$-$C_4$alkyl or $C_1$-$C_4$alkoxy, wherein the said phenyl, benzyl, pyridyl, furyl or pyrrolyl may have 1-3 substituents selected from the group consisting of halogen, —OH, —NH₂, $C_1$-$C_4$alkyl or $C_1$-$C_4$alkoxy.

$R_2'$ is selected from benzyl, mono-, di- or tri- halobenzyl, benzoyl, pyridylmethyl, pyridylmethoxy, phenoxy, mono-, di- or tri- halophenoxy or mono-, di- or tri-halophenylsulfonyl, furylmethyl, pyrrolylmethyl, pyrrolylmethoxy, halogen, $C_1$-$C_4$alkyl or $C_1$-$C_4$alkoxy, wherein the said phenyl, benzyl, pyridyl, furyl or pyrrolyl may have 1-3 substituents selected from the group consisting of halogen, —OH, —NH₂, $C_1$-$C_4$alkyl or $C_1$-$C_4$alkoxy.

The present invention also provides the use of the compounds of this invention in the production of anti-tumor medicament.

The present invention also provides a pharmaceutical composition which comprises 0.05-100 mg of a compound of formula I, or a pharmaceutically acceptable salt thereof, and a pharmaceutically acceptable carrier, excipient or diluent.

The present invention also provides a method for treating tumor, especially the tumor mediated by protein tyrosine kinases, which comprises the step of administering to a patient in need of such treatment 0.05-100 mg/kg of body weight daily a compound of formula I, or a pharmaceutically acceptable salt, or a solvate thereof.

The present invention also provides a method for preparing a pharmaceutical composition, which comprises the step of mixing a compound of formula I, or a pharmaceutically acceptable salt, or a solvate thereof with a pharmaceutically acceptable carrier, excipient or diluent, thereby a pharmaceutical composition is formed.

In another preferred embodiment, $R_2$ is selected from benzyloxy, mono-, di- or tri-halobenzyloxy; and $R_2'$ is halogen.

In another preferred embodiment, $R_1$ is selected from halogen, $C_1$-$C_4$alkoxy, $C_1$-$C_4$alkoxy substituted by halogen, methoxyethoxy, N-morpholinopropoxy, ester group, acylamino, sulfonamide group, phenyl, furyl, or $R_1$ is

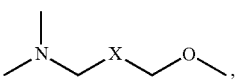

wherein X is furyl.

In another preferred embodiment, $R_1$ is an acylamino as follows:

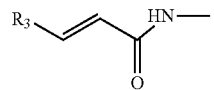

Wherein $R_3$ is selected from hydrogen, N,N-dimethyl aminomethyl, N,N-diethylaminomethyl, N,N-dipropylaminomethyl or N-morphlinomethyl.

In another preferred embodiment, $R_1$ is an acylamino as follows:

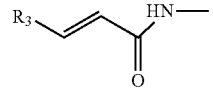

Wherein $R_3$ is selected from hydrogen or N,N-dimethyl aminomethyl.

In another preferred embodiment, $R_1$ is selected from α,β-unsaturated sulfonamide or aryl sulfonamide, or $R_1$ is selected from a phenyl substituted by alkyl, alkoxy, alkoxymethyl, ester group, sulfonate, or hydroxymethyl.

In another preferred embodiment, $R_1$ is selected from a phenyl substituted by alkoxy, alkoxymethyl, ester group, or hydroxymethyl.

The preferred compounds of this invention are selected from the group consisting of:
N-{4-[3-chloro-4-(3-fluorobenzyloxy)-phenylamino]-quinazolin-6-yl}-acrylamide,
N-{4-[3-chloro-4-(3-fluorobenzyloxy)-phenylamino]-quinazolin-6-yl}-4-methylbenzenesulfonamide;
N-{4-[3-chloro-4-(3-fluorobenzyloxy)-phenylamino]-quinazolin-6-yl}-E,4-(dimethylamino)-but-2-enamide;
N-[4-(3-chloro-4-benzyloxy-phenylamino)-quinazolin-6-yl]-E,4-(dimethylamino)-but-2-enamide;
N-{4-[3-chloro-4-(3-fluorobenzyloxy)-phenylamino]-7-trifluoro ethoxy-quinazolin-6-yl}-E,4-(dimethylamino)-but-2-enamide;
N-{4-[3-chloro-4-(3-fluorobenzyloxy)phenylamino]-7-methoxy-quinazolin-6-yl}-E,4-(dimethylamino)-but-2-enamide;
N-{4-[3-chloro-4-(3-fluorobenzyloxy)-phenylamino]-7-methoxy-quinazolin-6-yl}-acrylamide;
N-{4-[3-chloro-4-(3-fluorobenzyloxy)-phenylamino]-7-chloro-quinazolin-6-yl}-E,4-(dimethylamino)-but-2-enamide;
N-{4-[3-chloro-4-(3-fluorobenzyloxy)-phenylamino]-7-chloro-quinazolin-6-yl}-acrylamide;
O-{4-[3-chloro-4-(3-fluorobenzyloxy)-phenylaminio]-quinazolin-6-yl}-acetate;
4-[3-chloro-4-(3-fluorobenzyloxy)-phenylamino]-6-hydroxy-quinazoline;
4-[3-chloro-4-(3-fluorobenzyloxy)-phenylamino]-6-(3-oxo-butoxy-quinazoline;
4-[3-chloro-4-(3-fluorobenzyloxy)-phenylamino]-6-[3-(4-morpholine)-propoxy]-quinazoline;
4-[3-chloro-4-(3-fluorobenzyloxy)-phenylamino]-6,7-dimethoxy-quinazoline;
4-[3-chloro-4-(3-fluorobenzyloxy)-phenylamino]-6-bromo-quinazoline;
4-[3-chloro-4-(3-fluorobenzyloxy)-phenylamino]-6-(4-methoxy-phenyl)-quinazoline;

4-[3-chloro-4-(3-fluorobenzyloxy)-phenylamino]-6-(3-hydroxymethyl-phenyl)-quinazoline;

4-[3-chloro-4-(3-fluorobenzyloxy)-phenylamino]-6-(3-acetoxymethyl-phenyl)-quinazoline;

4-[3-chloro-4-(3-fluorobenzyloxy)-phenylamino]-6-[3-(3-oxo-butoxy-methyl)-phenyl]-quinazoline;

4-[3-chloro-4-(3-fluorobenzyloxy)-phenylamino]-6-(5-hydroxymethyl-furan-2-yl)-quinazoline;

4-[3-chloro-4-(3-fluorobenzyloxy)-phenylamino]-6-(5-methanesulfonyloxymethylene-furan-2-yl)-quinazoline;

4-[3-chloro-4-(3-fluorobenzyloxy)-phenylamino]-6-(5-dimethylaminomethyl-furan-2-yl-methoxy)-quinazoline or 4-[3-chloro-4-(3-fluorobenzyloxy)-phenylamino]-6-(3-(4-morpholino)propoxy]-7-methoxy-quinazoline.

DETAILED DESCRIPTION OF THE INVENTION

Figure 1:
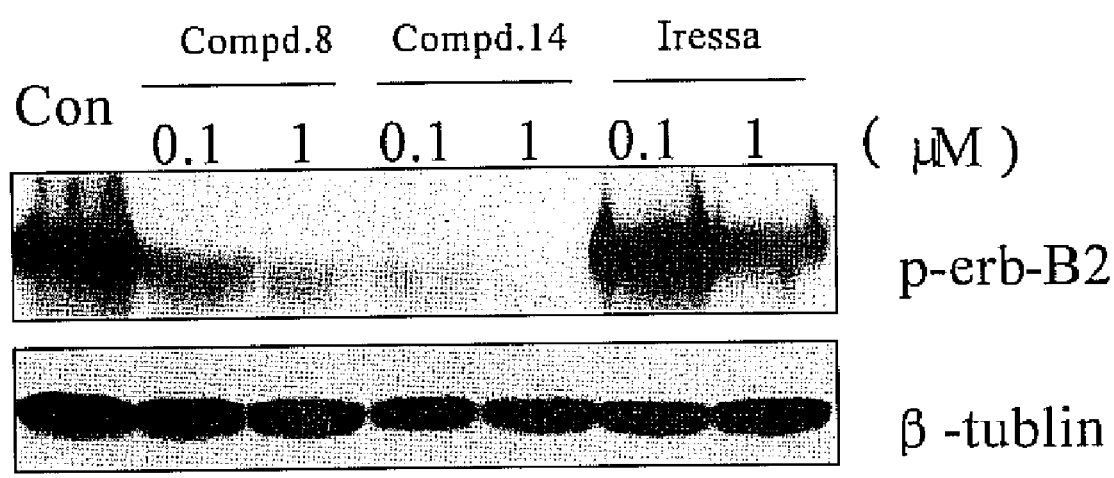
FIG. 1 shows the inhibitory effect of the compound of this invention against the phosphorylation of Erb-B2 kinases.

In the present invention,

The term "halogen" includes fluoro, chloro, bromo or iodo, preferably fluoro, chloro and bromo.

The term "$C_1$-$C_4$alkyl" includes methyl, ethyl, propyl, isopropyl, butyl, isobutyl, sec-butyl or tert-butyl, preferably methyl, ethyl, propyl, isopropyl or butyl, more preferably methyl.

The term "$C_1$-$C_4$alkoxy" includes methoxy, ethoxy, n-propoxy, isopropoxy, n-butoxy, isobutoxy, sec-butoxy or tert-butoxy, preferably methoxy, ethoxy, propoxy, isopropoxy or butoxy, more preferably methoxy.

The term "ester group" includes formate, acetate, propionate or butyrate, preferably acetate.

The term "acylamino" includes formamido, acetamido, propionamido; preferably α,β-unsaturated propionamide.

The term "sulfonamide group" includes methanesulfonylamino, ethanesulfonylamino, propanesulfonylamino, isopropanesulfonylamino; preferably methanesulfonylamino.

The term "phenyl" includes unsubstituted or substituted phenyl, wherein the substituents are 1-3 substituents selected from halogen, —OH, $C_1$-$C_4$alkyl, $C_1$-$C_4$alkoxy, $C_1$-$C_4$ alkyl-OH, $C_1$-$C_4$alkoxymethyl, $C_2$-$C_4$ester group, or sulfonate, preferably phenyl substituted by alkyl, alkoxy, alkoxymethyl, ester group, sulfonate or hydroxymethyl, more preferably phenyl substituted by alkoxy, alkoxymethyl, ester group and/or hydroxymethyl.

The term "furyl" includes unsubstituted or substituted furyl, wherein the substituents are 1-3 substituents selected from halogen, —OH, —NH$_2$, $C_1$-$C_4$alkyl, $C_1$-$C_4$alkoxy, alkoxymethyl, $C_2$-$C_4$ester group, or sulfonate, preferably furyl substituted by alkyl, alkoxy, alkoxymethyl, ester group, sulfonate and/or hydroxyl.

The term "thienyl" includes unsubstituted or substituted thienyl, wherein the substituents are 1-3 substituents selected from halogen, —OH, —NH$_2$, $C_1$-$C_4$alkyl, $C_1$-$C_4$alkoxy, alkoxymethyl, $C_2$-$C_4$ester group, or sulfonate, preferably thienyl substituted by alkyl, alkoxy, alkoxymethyl, ester group, sulfonate, and/or hydroxyl.

The present invention also provides the method for the preparation of a compound of formula I. Generally, the compounds of the present invention may be prepared by the nucleophilic reaction between a substituted quinazoline intermediate and 3-chloro-4-(m-fluorobenzyloxy)-aniline in an organic solvent. The reaction is usually conducted under reflux. After large amount of solid has been deposited, the mixture is filtered, and the filter cake is washed with a small quantity of ethyl acetate and dried under vacuum at 60° C. overnight to obtain the compound of the present invention.

In the preparation method of the present invention, every reaction is conducted at a temperature between −10° C. and refluxing temperature. Usually the reaction temperature ranges from the room temperature (about 25° C.) to a refluxing temperature, preferably 5 to 100° C., more preferably 20 to 80'. There is no limitation to the reaction time, generally from 1 min to 24 h, preferably from 1 to 20 hours. The solvent used in the reaction is usually inert, such as water, DMF, alcohol (for example methanol, ethanol and isopropanol).

The compounds of the present invention may be administered to human and animals, which may be administered via oral, rectal, parenteral (e.g., intravenous, intramuscular or subcutaneous), local (e.g., powders, ointments or drops), or intratumor. The mentioned compounds may be administered separately or in conjunction with other pharmaceutically acceptable compounds. It is appreciated that the compounds of the present invention can be administrated as a mixture.

The solid dosage form suitable for oral use may include capsules, tablets, pills, powders or granules. In such solid dosage form, the active ingredient may be mixed with at least one conventional inert excipient (or carrier), such as sodium citrate or dicalcium phosphate; or with a component selected from:

(a) fillers or solubilizers, for example, starch, lactose, sucrose, glucose, mannitol or silicic acid; (b) binders, for example, hydroxymethyl cellulose, alginate, gelatin, polyvinylpyrrolidone, sucrose and acacia; (c) humectants, for example glycerol; (d) disintegrants, such as agar, calcium carbonate, potato starch or tapioca starch, alginic acid, certain composite silicates or sodium carbonate; (e) retarding solvents, for example, olefin; (f) absorbent accelerators, such as quaternary ammonium compounds; (g) moistening agents, such as cetyl alcohol and glycerol monostearate; (h) absorbing agents, such as kaolin; and (i) lubricants, such as talc, calcium stearate, magnesium stearate, solid Polyethylene Glycol, Sodium dodecylsulfate or the mixture thereof. A buffer can also be contained in the dosages forms such as capsules, tablets or pills.

Solid dosage forms, such as tablets, rotulas, capsules, pills and granules may be prepared from coatings and shells such as enteric coatings or other materials known to those skilled in the art. They can include opaque materials. Furthermore, active compounds or compounds in the composition can be released into certain part of the alimentary canal in a delayed manner. Examples of usable embedding components include polymers and waxy substance. If necessary, the active compounds can also be combined with one or more of excipients above to form micro-capsules.

Liquid dosage forms for oral administration may include pharmaceutically acceptable emulsions, solutions, suspensions, syrups, injections or tinctures. Beside active compounds, the liquid dosage form may include inert diluents conventionally used in this field, such as water or other solvents, solubilizing agents and emulsifying agents, such as ethanol, isopropanol, ethyl carbonate, ethyl acetate, propylene glycol, 1,3-butanediol, dimethylformamide and oil, in particular cottonseed oil, peanut oil, corn germ oil, olive oil, caster oil and sesame oil or the mixture thereof.

Beside the inert diluents, the composition may also include auxiliary agents such as moistening agents, emulsifying agents and suspending agents, sweetening agents, flavoring agents and flavors.

Beside the active compounds, the suspensions may include suspending agents, for example, ethoxylated isooctadecanol, polyoxyethylene sorbitol, and dehydrated sorbate, microcrystalline cellulose, methanol aluminium, agar, or mixtures thereof.

Compositions for parenteral injection may include physiologically acceptable sterile solutions, dispersions, suspensions or emulsions with or without water, and sterile powders for being reconstituted into sterile injectable solutions or dispersions. Appropriate aqueous or non-aqueous carriers, diluents, solvents or excipients may include water, ethanol, polyol and appropriate mixtures thereof.

Dosage forms of the compounds of the invention for local administration may include ointments, powders, sprays and inhalants. The active component is mixed with physiologically acceptable carriers and any antiseptics, buffers, or required propellants if necessary under sterile condition.

In the present invention, the term "pharmaceutically acceptable salts" means relatively innocuous inorganic acid addition salts or organic acid addition salts of the compound of the present invention. These salts may be prepared in situ during the final isolation and purification of the compounds; or prepared by reacting the purified compounds in a form of free alkali with appropriate organic or inorganic acids and isolating the salts formed. Representative salts includes hydrobromide, hydrochloride, sulfate, sulphite, acetate, oxalate, pentanoate, oleate, palmate, stearate, laurate, borate, benzoate, lactate, phosphate, toluene formate, citrate, maleate, fumarate, succinate, tartrate, benzoate, methanesulfonate, gluconate, lactobionate and laurylsulfonate and the like. They may contain cations based on alkali metals and alkali-earth metals, such as sodium, lithium, potassium, calcium, magnesium and the like, and cations of innocuous amine, quarternary amine, and amine cations, including but not limited to amine, tetramethyl amine, tetraethyl amine, methyl amine, dimethyl amine, trimethyl amine, triethylamine, ethylamine and the like.

The compounds of the present invention can be used to treat a disease mediated by a protein tyrosine kinase, such as breast cancer, non-small cell lung cancer, ovarian cancer, stomach cancer, pancreatic cancer and so on.

The advantage of the present invention lies in that the compounds of the present invention possess excellent anti-tumor activity and notable inhibitory activity against phosphorylation of Erb-B12.

In conjunction with the following preferred embodiments, the invention will be further illustrated. It is appreciated that the examples are illustrative only and would not intend to limit the extent of the invention. The experiment methods which have been noted without specific conditions are generally carried out in accordance with conventional conditions, or in accordance with the conditions as instructed by the manufacturers. Unless otherwise indicated, the parts and percents are by weight.

EXAMPLES

Example 1

3-chloro-4-(3-fluorobenzyloxy)-aniline

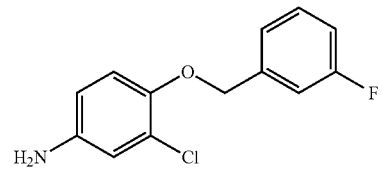

In a 250 mL flask equipped with a reflux condenser, 2-chloro-4-nitrophenol 4.65 g (26.6 mmol), 1-(bromomethyl)-3-fluorobenzene 3.3 mL (27.0 mmol, 1 eq), $K_2CO_3$ 9.4 g (54 mmol, 2 eq) and 50 mL of DMF were added and then heated to reflux. The mixture was stirred for 4 h, and then filtered without cooling to remove the solid. The filtrate was cooled to room temperature. 300 mL of ethyl acetate was added to dilute the solution, and washed with water for 3 times. The organic phases were combined, dried and concentrated. The resulting residue was purified by column chromatography to obtain a solid product.

The above solid product was added into a 250 ml flask equipped with a reflux condenser, reduced iron power 4.7 g (87 mmol), 10 mL of acetic acid and 50 mL of absolute ethanol were then added. The mixture was stirred under reflux for 5 h, then cooled to room temperature, and extracted with large amount of mixed solvent comprised of water and ethyl acetate. The organic phases were combined, washed with $NaHCO_3$ solution for 2 times, dried and concentrated. The resulting residue was purified by column chromatography to obtain the title compound as brown solid, total yield: 75%.

$^1$H-NMR (400 MHz, $CDCl_3$): δ7.38-7.29(1H, m), 7.23-7.16(2H, m), 7.04-6.96(1H, m), 6.79-6.74(2H, m), 6.50(1H, dd, J=2.75 Hz, 8.61 Hz), 5.03(2H, s), 3.50(2H, br).

Example 2

3-chloro-4-benzyloxy-aniline

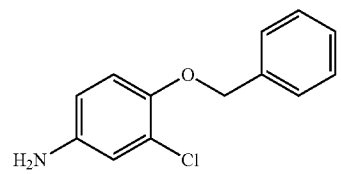

In a 250 mL flask equipped with a reflux condenser, 2-chloro-4-nitrophenol 4.65 g (26.6 mmol), benzyl bromide 2.97 mL (27.0 mmol, 1 eq), $K_2CO_3$ 9.4 g (54 mmol, 2 eq) and DMF (60 mL) were added and then heated to reflux. The procedure was conducted as Example 1, the residue was purified by column chromatography to obtain the title compound as brown solid, total yield: 73%.

¹H-NMR (400 MHz, CDCl₃): δ7.30-7.28(1H, m), 7.23-7.16(2H, m), 7.04-6.96 (1H, m), 6.79-6.74(2H, m), 6.50(1H, dd, J=2.75 Hz, 8.61 Hz), 5.03(2H, s), 3.50(2H, br).

Example 3

4-chloro-6-nitro-quinazoline

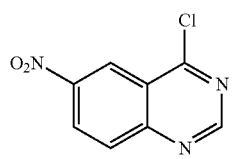

In a 100 mL flask equipped with a reflux condenser, 6-nitro-quinazolin-4-one 2.85 g (15 mmol), phosphoryl chloride 25 mL were added. The mixture was stirred at 105° C. for 3 h, and then was dropped into 150 mL of ice water carefully, the squama solid deposited was filtered out, dried, and identified as the title compound. Yield: 78%.

¹H-NMR (400 MHz, CDCl₃): δ9.22(2H, s), 8.74(1H, dd, J=2.57 Hz, 9.16 Hz), 8.27(1H, d, J=9.16 Hz).

Example 4

4-chloro-6,7-dimethoxy-quinazoline

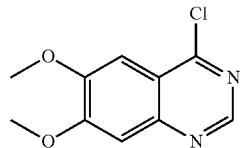

In a 100 mL flask equipped with a reflux condenser, 6,7-dimethoxy-quinazolin-4-one 4.5 g (20 mmol), phosphoryl chloride (45 ml) were added. The mixture was stirred at 105° C. for 2 h, and then was poured into 100 mL of ice water carefully, and off-white squama solid was deposited slowly, which was filtered, dried and identified as the title compound. Yield: 80%.

¹H-NMR (400 MHz, DMSO): δ8.89(1H, s), 7.47(1H, s), 7.41(1H, s), 4.02(3H, s), 4.00(3H, s).

Example 5

O-(4-chloroquinazolin-6-yl)acetate

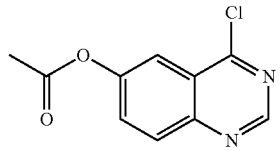

In a 100 mL flask equipped with a reflux condenser, 6-acetoxyquinazolone 3.06 g (15 mmol), phosphoryl chloride. (35 mL) were added. The mixture was refluxed at 105° C. for 2 h, and then was taken out and poured into 150 mL of ice water carefully. A large amount of solid was deposited slowly, which was filtered, dried, and identified as the title compound. Yield: 74%.

¹H-NMR (400 MHz, CDCl₃): δ9.05(1H, s), 8.11(1H, d, J=9.06 Hz), 8.01(1H, d, J=2.52 Hz), 7.73(1H, dd, J=2.52 Hz, 9.06 Hz), 2.40(3H, s).

Example 6

4-[3-chloro-4-(3-fluoro-benzyloxy)-phenylamino]-6-nitro-quinazoline

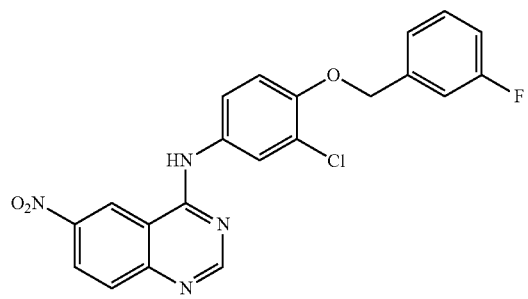

In a flask equipped with a reflux condenser, 6-nitro-4-chloro-quinazoline 1.20 g (5.7 mmol) and 4-(3-fluorobenzyloxy)-3-chloroaniline 1.37 g (5.6 mmol) were dissolved into 80 mL of isopropanol, and the solution was refluxed for 3 h. Then a lot of yellow solid was deposited, which was filtered, dried under vacuum, and identified as the title compound. Yield: 67%.

¹H-NMR (400 MHz, CDCl₃): δ11.30(1H, br), 9.54-9.48 (1H, m), 8.45-8.41(1H, m), 8.31-8.25(1H, m), 7.98-7.89(1H, m), 7.50-7.47(1H, m), 7.35-7.26(1H, m), 7.05-6.96(1H, m), 6.90-6.80(2H, m), 7.74-7.60(2H, m), 4.84(2H, s).

Example 7

4-[3-chloro-4-(3-fluoro-benzyloxy)-phenylamino]-6-amino-quinazoline

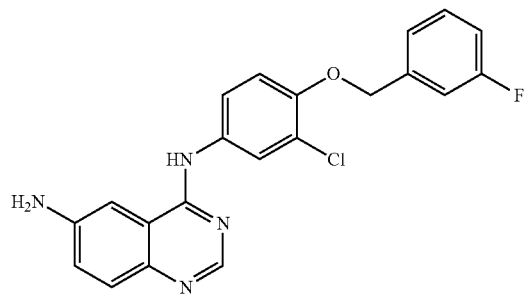

In a flask equipped with a reflux condenser, the compound obtained in Example 6 1.60 g (3.77 mmol), reduced iron powder 1.05 g (18.85 mmol, 5 eq), glacial acetic acid (2 mL) and methanol (40 mL) were mixed. The mixture was refluxed in an oil bath at a temperature of 85° C. for 2.5 h. Then the iron powder was filtered of, the filtrate was diluted with ethyl acetate, washed sequentially with NaHCO₃ solution and water. The organic phase was dried and concentrated to obtain yellow solid, which was identified as the title compound. Yield: 61%.

$^1$H-NMR (400 MHz, DMSO): δ9.32(1H, s), 8.31(1H, s), 8.04(1H, d, J=2.64 Hz), 7.73(1H, dd, J=2.64 Hz, 8.80 Hz), 7.54-7.43(2H, m), 7.36-7.28(3H, m), 7.26-7.14(3H, m), 5.57 (2H, br), 5.27(2H, s).

Example 8

N-{4-[3-chloro-4-(3-fluorobenzyloxy)-phenylamino]-quinazolin-6-yl}-acrylamide

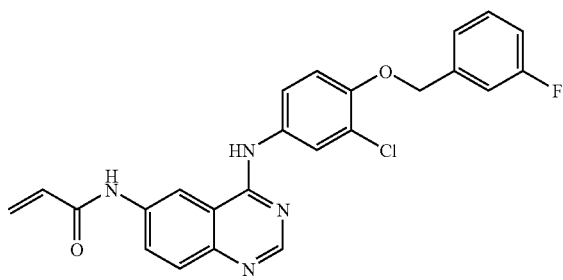

In a 100 mL flask cooled with an ice-bath, the amino-compound obtained in Example 7 1.2 g (3.04 mmol), triethylamine 0.61 mL (4.2 mmol, 1.5 eq), acrylic chloride 0.25 mL (3.04 mmol, 1 eq) and THF (40 mL) were added. The mixture was warmed to room temperature slowly, and three hours later, the reaction was stopped. The reactants were extracted with the mixed system of ethyl acetate-water, and the organic phases were combined, dried and concentrated. The resulting residue was purified by the silica gel column chromatography to obtain 10 g of solid, which was identified as the title compound. Yield: 67%.

$^1$H-NMR (400 MHz, CDCl$_3$+DMSO): δ68.75(1H, s), 8.60-8.52(2H, m), 7.81(1H, d, J=2.44 Hz), 7.69(2H, s), 7.54 (1H, dd, J=2.56 Hz, 8.92 Hz), 7.30-7.22(2H, m), 7.18-7.08 (2H, m), 6.96-6.86(2H, m), 6.37(2H, d, J=5.86 Hz), 5.67(1H, t, J=5.86 Hz), 5.06(2H, s).

Example 9

N-{4-[-3-chloro-4-(3-fluorobenzyloxy)-phenylamino]-quinazolin-6-yl}-p-methylbenzenesulfonamide

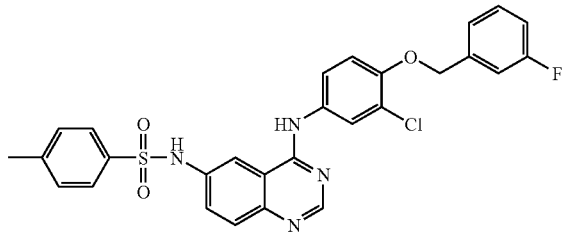

In a 50 mL flask cooled with an ice-bath, the amino-compound obtained in Example 7 1.2 g (3.04 mmol), triethylamine 1.22 mL (8.4 mmol, 3 eq), p-toluene sulfonyl chloride 0.25 mL (3.04 mmol, 1 eq) and THF (40 mL) were added. The mixture was warmed to room temperature slowly, and three hours later, the reaction was stopped. The reactants were extracted with the mixed system of ethyl acetate-water, and the organic phases were combined, dried and concentrated. The resulting residue was purified by the silica gel column chromatography to obtain 1.0 g of solid, which was identified as the title compound. Yield: 67%.

$^1$H-NMR (400 MHz, DMSO): δ9.52(1H, s), 8.45(1H, s), 8.09(1H, d, J=2.61 Hz), 7.95-7.88(3H, m), 7.82-7.77(2H, m), 7.64(1H, d, J=8.80 Hz), 7.55-7.44(3H, m), 7.35-7.15(5H, m), 5.25(2H, s), 3.05(3H, s).

Example 10

N-{4-[3-chloro-4-(3-fluorobenzyloxy)-phenylamino]-quinazolin-6-yl}-E,4-(dimethylamino)-but-2-enamide

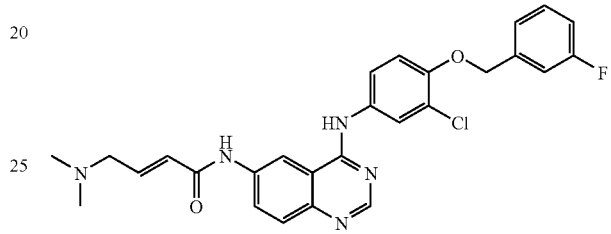

In a 50 mL flask, 3-N,N-(dimethylamino)-methylacrylic chloride 0.4 g (2.7 mmol) was dissolved into anhydrous THF (10 mL). The solution of the aryl amine obtained in Example 1 1.06 g (2.7 mmol) in 15 mL of anhydrous THF was added into the flask dropwise with strong stirring at 0° C., then the solution of 0.2 mL of diisopropylethylamine in 5 mL THF was added dropwise with the temperature being kept at 0° C. The mixture was stirred vigorously in an ice-water bath for 3 hours. Then extracted with the mixed system of ethyl acetate and water, the water phase was washed with ethyl acetate-THF for 3 times, and the organic phases were combined, dried and concentrated. The resulting residue was purified by the silica gel column chromatography to obtain 0.73 g of solid, which was identified as the title compound. Yield: 54%.

$^1$H-NMR (400 MHz, CDCl$_3$+DMSO): δ8.77(1H, s), 8.61-8.52(2H, m), 7.80(1H, d, J=2.44 Hz), 7.69(2H, s), 7.55(1H, dd, J=2.54 Hz, 8.90 Hz), 7.32-7.24(2H, m), 7.18-7.08(2H, m), 7.00-6.86(3H, m), 6.21(1H, dt, J=1.56 Hz, 15.65 Hz), 5.10(2H, s), 3.07(2H, d, J=7.14 Hz), 2.18(6H, s).

Example 11

N-[4-(3-chloro-4-benzyloxy-phenylamino)-quinazolin-6-yl]-E-4-(dimethylamino)-but-2-enamide

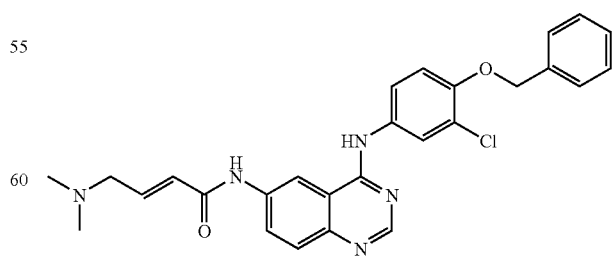

The procedure in Example 10 was repeated except that the substituted aryl amine in Example 10 was replace by the compound obtained in Example 2. 0.67 g of solid was obtained after silica gel column chromatography, which was identified as the title compound. Yield: 51%.

$^1$H-NMR (400 MHz, CDCl$_3$+DMSO): δ8.76(1H, s), 8.60-8.52(2H, m), 7.82(1H, d, J=2.45 Hz), 7.69(2H, s), 7.55(1H, dd, J=2.56 Hz, 902 Hz), 7.32-7.24(2H, m), 7.18-7.06(3H, m), 7.00-6.86(3H, m), 6.18(1H, dd, J=1.56 Hz, 15.65 Hz), 5.08 (2H, s), 3.10(2H, d, J=7.14 Hz), 2.21(6H, s).

Example 12

N-{4-[3-chloro-4-(3-fluorobenzyloxy)-phenylamino]-7-trifluoro ethoxy)-quinazolin-6-yl}-E-4-(dimethylamino)-but-2-enamide

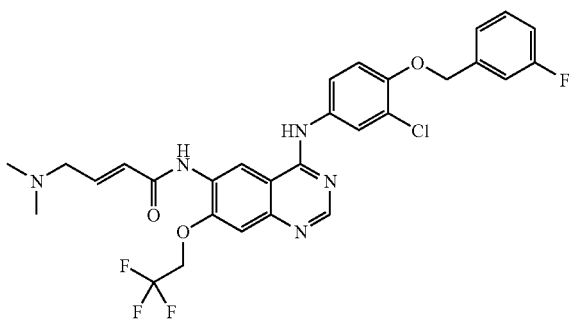

4-chloro-2-amino-benzoic acid (10.0 g) was dissolved into 50 mL of formamide, the mixture was reacted under reflux for 5 h. A lot of solid was deposited, which was filtered and dried to obtain 1.5 g of 7-chloro-quinazolone.

10 g of the above 7-chloro-quinazolone was added into a mixed acid of concentrated sulphuric acid and fuming nitric acid (40 ml) slowly in an ice-bath. Then the mixture was heated to 90° C. and reacted at this temperature for 3 h. The clear solution formed was then poured into 300 mL of ice-water carefully, and yellow solid was deposited, which was filtered, washed with water and redissolved into hot acetic acid, to deposit the crystalline of 6-nitro-7-chloro-quinazolone, which was collected and 6.50 g of the product was achieved.

4.00 g of the above crystalline 6-nitro-7-chloro-quinazolone was refluxed with 15 mL of phosphoryl chloride for 2 h, then the reaction mixture was poured into ice water, filtered and dried to obtain the intermediate 6-nitro-4,7-dichloro-quinazoline; The intermediate was dissolved into 30 mL of isopropanol, and 3.00 g of 3-chloro-4-(m-fluoro-benzyloxy)-aniline was added. The reaction mixture was reacted under reflux for 2 h and a lot of solid was deposited, which was filtered and dried under vacuum to obtain the solid product of 6-nitro-7-chloro-4-amino substituted quinazoline (3.83 g).

2.00 g of above intermediate was dissolved into 50 mL of anhydrous THF, and sodium trifluoroethanoxide (0.64 g) was then added, the reaction mixture was reacted under reflux for 16 h, and 1.78 g of 6-nitro-7-trifluoroethoxy-4-amino substituted quinazoline was obtained after post treatment.

The above obtained trifluoroethoxy substituted intermediate (1.6 g), reduced iron powder 1.05 g (17.85 mmol, 5 eq), glacial acetic acid (2 mL) and methanol (40 mL) were reacted under reflux in an oil-bath for 2.5 h, then filtered to remove the Fe powder. The filtrate was diluted with ethyl acetate, washed sequentially with NaHCO$_3$ solution and water. The organic phase was dried and concentrated to obtain 0.90 g of yellow solid, which was identified as 6-amino-7-trifluoroethoxy-4-amino substituted quinazoline. Yield: 61%.

In a 50 mL flask, the above reduced aryl amine (0.50 g) was dissolved into anhydrous THF (30 mL), diisopropylethylamine (0.18 mL) and 3-N,N-dimethylaminomethylacrylic chloride 0.17 g (1.1 mmol) were added dropwise sequentially at 0° C. The reaction was kept at 0° C. for 3 h. The reaction mixture was extracted with a mixed system of ethyl acetate and water, the aqueous phase was washed 3 times with ethyl acetate. The organic phases were combined, dried and concentrated. The resulting residue was purified by the silica gel column chromatography to obtain the title compound as a solid (0.45 g, 72%).

$^1$H-NMR (400 MHz, CDCl$_3$): δ8.77(1H, s), 8.61-8.52(2H, m), 7.80(1H, d, J=2.46 Hz), 7.69(2H, m), 7.55(1H, dd, J=2.56 Hz, 8.94 Hz), 7.32-7.24(1H, m), 7.18-7.08(2H, m), 7.00-6.86 (3H, m), 6.23(1H, dd, J=1.55 Hz, 15.59 Hz), 5.10(2H, s), 4.48(2H, m), 3.11(2H, d, J=7.15 Hz), 2.19(6H, s).

Example 13

N-{4-[3-chloro-4-(3-fluorobenzyloxy)-phenylamino]-7-methoxy-quinazolin-6-yl}-E-4-(dimethylamino)-but-2-enamide

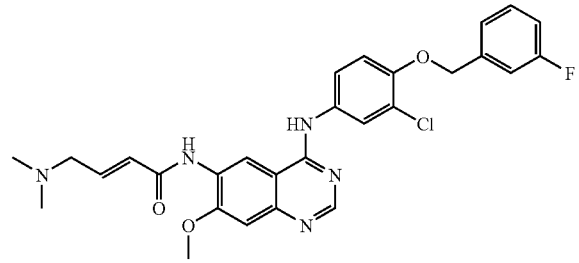

The procedure of Example 12 was repeated except that 6-nitro-7-chloro-4-[3-chloro-4-(3-fluorobenzyloxy)phenylaminoquin azoline is reacted with the sodium methoxide-methanol system instead of trifluoroethanol sodium to achieve 6-nitro-7-methoxy-4-[3-chloro-4-(3-fluorobenzyloxy)phenylaminoquinazoline as the intermediate; The nitro group of the intermediate was reduced and then reacted with 3-N,N-dimethylaminomethylacrylic chloride to obtain the title compound after purification.

$^1$H-NMR (400 MHz, CDCl$_3$). δ9.80(1H, s), 9.70(1H, s), 8.91(1H, s), 8.50(1H, s), 7.98(1H, d, J=2.44 Hz), 7.69(1H, dd, J=2.44 Hz, 9.16 Hz), 7.51-7.42(1H, m), 7.39-7.16(5H, m), 6.90-6.87(1H, m), 6.19(1H, dd, J=2.14 Hz, 10.06 Hz), 5.27 (2H, s), 4.02(3H, s), 3.07(2H, d, J=3.8 Hz), 2.18(6H, s).

Example 14

N-{4-[3-chloro-4-(3-fluorobenzyloxy)-phenylamino]-7-methoxy-quinazolin-6-yl}-acrylamide

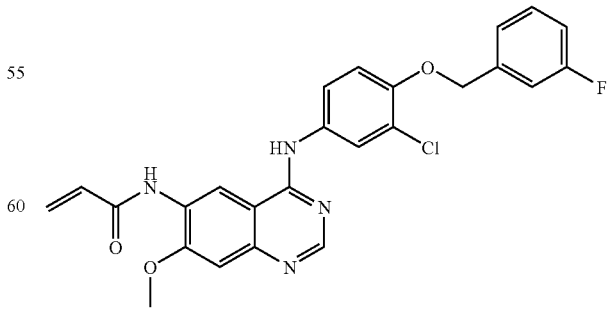

The procedure of Example 12 was repeated except that 6-nitro-7-chloro-4-[3-chloro-4-(3-fluorobenzyloxy)phenylamino quinazoline is reacted with the sodium methoxide-methanol system instead of trifluoroethanol sodium to achieve 6-nitro-7-methoxy-4-[3-chloro-4-(3-fluorobenzyloxy)phenylamino quinazoline as the intermediate; The nitro group of the intermediate was reduced and then reacted with acrylic chloride to obtain the title compound after purification.

¹H-NMR (300 MHz, CDCl₃): δ9.80(1H, s), 9.70(1H, s), 8.91(1H, s), 8.50(1H, s), 7.98(1H, d, J=2.44 Hz), 7.69(1H, dd, J=2.44 Hz, 9.16 Hz), 7.51-7.42(1H, m), 7.39-7.16(5H, m), 6.75(1H, q, J=10.06 Hz, 16.78 Hz), 6.31(1H, dd, J=2.14 Hz, 7.09 Hz), 5.80(1H, dd, J=2.14 Hz, 10.06 Hz), 5.27(2H, s), 4.02(3H, s).

Example 15

N-{4-[3-chloro-4-(3-fluorobenzyloxy)-phenylamino]-7-chloro-quinazolin-6-yl}-E,4-(dimethylamino)-but-2-enamide

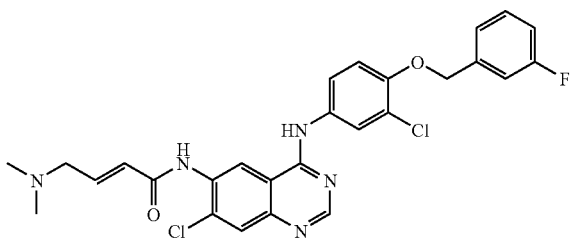

The procedure of Example 12 was repeated except that the nitro group in the intermediate 6-nitro-7-chloro-4-[3-chloro-4-(3-fluorobenzyloxy)phenylamino quinazoline was reduced into amino group directly and then the reduced intermediate was reacted with 4-(dimethylamino)-2-butenoyl chloride. Finally the title compound was purified.

Example 16

N-{4-[3-chloro-4-(3-fluorobenzyloxy)-phenylamino]-7-chloro-quinazolin-6-yl}-acrylamide

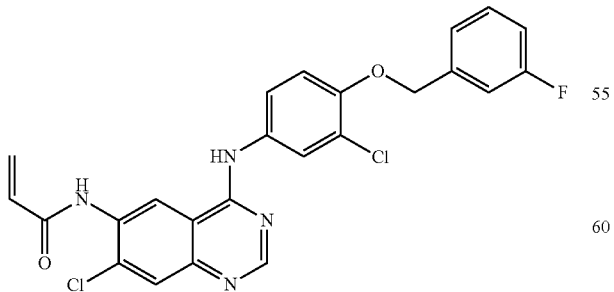

The procedure of Example 12 was repeated except that the nitro group in the intermediate 6-nitro-7-chloro-4-[3-chloro-4-(3-fluorobenzyloxy)phenylamino quinazoline was reduced into amino group directly and then the reduced intermediate was reacted with acryl chloride. the title compound was obtained after purification.

Example 17

O-{4-[-3-chloro-4-(3-fluorobenzyloxy)-phenylamino]-quinazolin-6-yl}-acetate

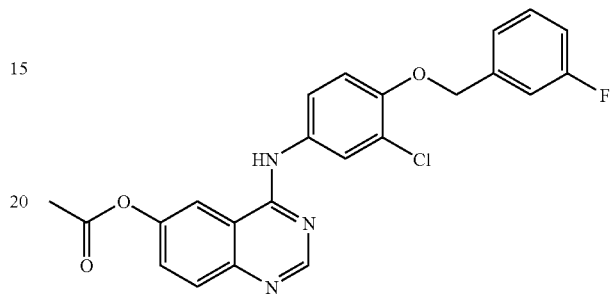

6-acetoxy-4-chloroquinazoline (0.90 g, 4.04 mmol) and 3-chloro-4-(m-fluoro-benzyloxy)-aniline (1.00 g, 3.97 mmol) were dissolved into 40 mL of isopropanol, and the mixture was stirred under reflux for 3 h. A lot of light grey solid was deposited, which was filtered, and the filter cake was washed with small quantity of ethyl acetate and dried under vacuum at 60° C. overnight to obtain the title compound (1.65 g, 95%).

¹H-NMR (400 MHz, CDCl₃): δ8.68(1H, s), 7.89-7.81(2H, m), 7.58-7.48(2H, m), 7.40-7.32(1H, m), 7.27-7.19(3H, m), 7.16(1H, d, J=2.46 Hz), 7.07-6.96(2H, m), 5.14(2H, s), 2.11 (3H, s).

Example 18

4-[3-chloro-4-(3-fluorobenzyloxy)-phenylamino]-6-hydroxy-quinazoline

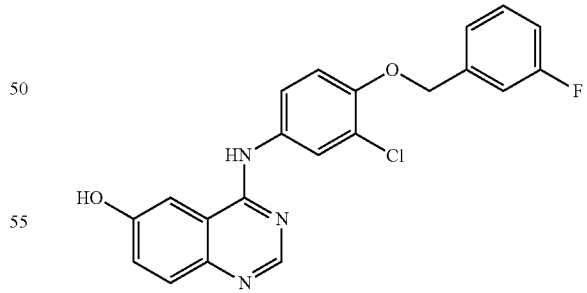

0.47 g of 6-acetoxy-4-aminoquinazoline intermediate was dissolved into 12 mL of methanol, and 1 ml of concentrated ammonia was added dropwise, then yellow solid was deposited immediately. The reaction was carried out at room temperature for 3 h, and then filtered to obtain part of the product. The filtrate was concentrated and purified through chromatography to obtain another part of product, total 0.41 g, yield 97%.

¹H-NMR (400 MHz, CDCl₃): δ8.68(1H, s), 7.88-7.81(2H, m), 7.58-7.48(2H, m), 7.40-7.32(1H, m), 7.27-7.19(3H, m), 7.16(1H, d, J=2.44 Hz), 7.07-6.96(2H, m), 5.15(2H, s).

Example 19

4-[3-chloro-4-(3-fluorobenzyloxy)-phenylamino]-6-(3-oxo-butoxy-quinazoline

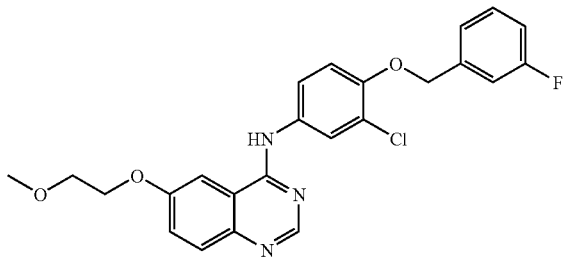

The 6-hydroxy-4-aminoquinazoline starting material 0.20 g and 2-methoxybromoethane 0.07 mL (1.5 eq.) were dissolved into 15 mL of DMF. A catalytic amount of tetrabutylammonium iodide and K₂CO₃ solid 0.14 g were added, the mixture was reacted at 60° C. overnight. The mixture was filtered without cooling, and the filtrate was concentrated to remove the solvent. The resulting residue was purified through column chromatography to obtain the title compound (0.17 g, 74%).

¹H-NMR (400 MHz, CDCl₃): δ8.67(1H, s), 7.88-7.81(2H, m), 7.56-7.47(2H, m), 7.41-7.32(1H, m), 7.27-7.19(3H, m), 7.15(1H, d, J=2.44 Hz), 7.06-6.96(2H, m), 5.16(2H, s), 4.29-4.24(2H, m), 3.85-3.81(2H, m), 3.49(3H, s).

Example 20

4-[3-chloro-4-(3-fluorobenzyloxy)-phenylamino]-6-[3-(4-morpholino)propoxy]-quinazoline

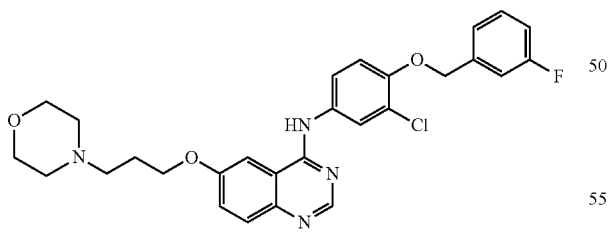

The procedure of Example 15 was repeated except that the starting material 6-hydroxy-4-amino quinazoline 0.10 g was reacted with excessive 3-(N-morpholino)-1-chloropropene to obtain the title compound (0.09 g, 70%).

¹H-NMR (400 MHz, CDCl₃): δ8.69(1H, s), 7.87-7.82(2H, m), 7.55(1H, dd, J=2.56 Hz, 8.87 Hz), 7.46(1H, dd, J=2.56 Hz, 9.17 Hz), 7.40-7.32(1H, m), 7.29-7.19(3H, m), 7.16(1H, d, J=2.49 Hz), 7.10-6.96(2H, m), 5.17(2H, s), 4.17(2H, t, J=6.45 Hz), 3.74(4H, t, J=4.69 Hz), 2.57(2H, t, J=7.18 Hz), 2.50(4H, t, J=4.61 Hz), 2.10-2.01(2H, m).

Example 21

4-[3-chloro-4-(3-fluorobenzyloxy)-phenylamino]-6,7-dimethoxy-quinazoline

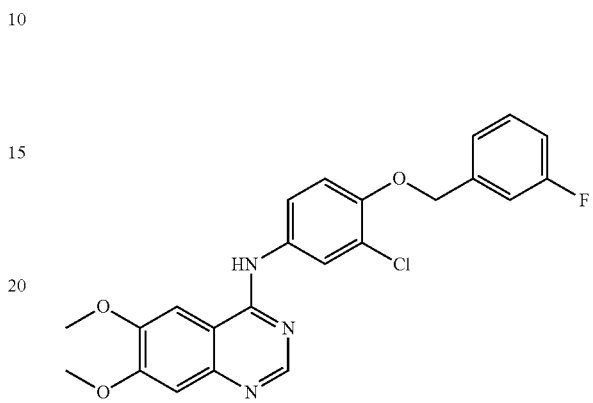

4-chloro-6,7-dimethoxy-quinazoline (1.50 g) and 3-choro-4-(m-fluoro-benzyloxy)-aniline (1.70 g) were dissolved into 150 mL of isopropanol. The mixture was reacted under reflux for 3 h, and a lot of yellow solid was deposited. The precipitated solid was filtered, and the filter cake was washed with cold ethanol and dried at 60° C. under vacuum overnight to obtain the title compound (2.50 g, 84%).

¹H-NMR (400 MHz, DMSO): δ11.30(1H, br), 8.83(1H, s), 8.25(1H, s), 7.86(1H, d, J=2.64 Hz), 7.62(1H, dd, J=2.63 Hz, 9.08 Hz), 7.52-7.44(4H, m), 7.23-15(1H, m), 5.30(2H, s), 4.01(3H, s), 3.99(3H, s).

Example 22

4-[-3-chloro-4-(3-fluorobenzyloxy)-phenylamino]-6-bromo-quinazoline

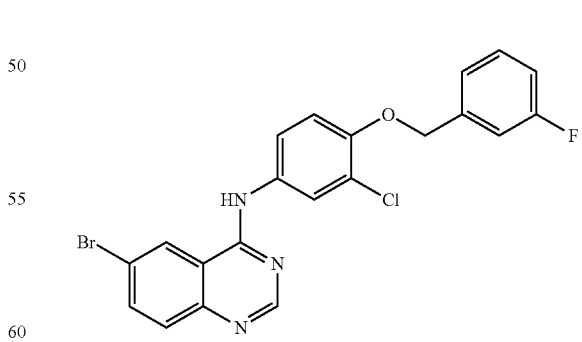

6-bormo-4-chloro-quinazoline (1.36 g) and 3-choro-4-(m-fluoro-benzyloxy)-aniline (1.42 g) were dissolved into 50 mL of isopropanol. The mixture was reacted under reflux for 3 h, and a lot of yellow solid was deposited. The precipitated solid was filtered, and the filter cake was washed with cold ethanol and dried at 60° C. under vacuum overnight to obtain the 6-bromo-4-aminoquinazoline product (2.20 g, 86%).

¹H-NMR (400 MHz, DMSO): δ11.33(1H, s), 9.07(1H, s), 8.94(1H, s), 8.25-8.16(1H, m), 7.94(1H, d, J=2.64 Hz), 7.85 (1H, d, J=9.09 Hz), 7.69-7.61(1H, m), 7.53-7.44(1H, m), 7.38-7.29(3H, m), 7.24-7.16(1H, m), 5.30(2H, s).

Example 23

4-[-3-chloro-4-(3-fluorobenzyloxy)-phenylamino]-6-(4-methoxy-phenyl)-quinazoline

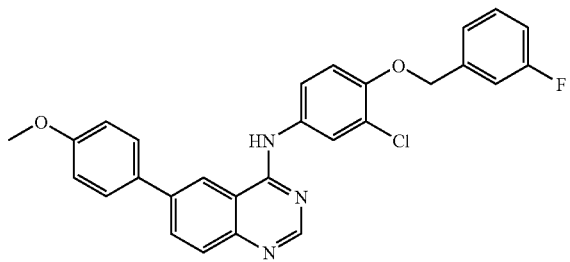

6-bromo-4-aminoquinazoline intermediate (0.30 g) and 4-methoxyphenyl boric acid (0.15 g) were dissolved into 20 mL of DMF. Then Pd (PPh$_3$)4(0.15 g) and Na$_2$CO$_3$ (0.14 g) were added thereto under nitrogen atmosphere, and the mixture was reacted at 60° C. for 3 h. The solvent was removed under reduced pressure, and the resulting residue was purified by column chromatography to obtain the 6-(4-methoxy-phenyl)-4-amino substituted quinazoline product (0.21 g, 66%).

¹H-NMR (400 MHz, CDCl$_3$): δ8.78(1H, s), 8.04-7.89(3H, m), 7.85(1H, d, J=2.75 Hz), 7.63-7.53(3H, m), 7.46(1H, m), 7.40-7.32(1H, m), 7.27-7.19(2H, m), 7.06-6.96(4H, m), 5.19 (2H, s), 3.88(3H, s).

Example 24

4-[3-chloro-4-(3-fluorobenzyloxy)-phenylamino]-6-(3-hydroxymethyl-phenyl)-quinazoline

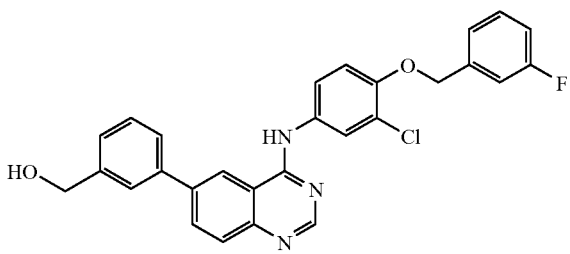

6-bromo-4-amino substituted quinazoline intermediate (1.50 g) and 3-formylphenyl boric acid (1.37 g) were dissolved into 100 mL of 1,4-dioxane. Then Pd(PPh$_3$)4(0.76 g) and 20% aqueous K$_2$CO$_3$ solution (5 mL) were added thereto under nitrogen atmosphere, and the mixture was reacted at 60° C. for 0.5 h. The solvent was removed under reduced pressure, and the resulting residue was purified by column chromatography to obtain a 6-(3-formylphenyl-4-amino substituted quinazoline intermediate (1.45 g).

The above intermediate was dissolved into a mixed solvent of THF/MeOH (2:1). 0.12 g of NaBH$_4$ solid was added thereto at 0° C. in portions while stirring, and the reaction system turned dark gradually. 30 min later, most solvent was removed under reduced pressure, and the resulting residue was dissolved into ethyl acetate, the organic phase was washed with saturated saline, dried and purified by silica gel column chromatography to obtain the title compound (0.82 g, the total yield of the two steps is 51%).

¹H-NMR (400 MHz, DMSO+CDCl$_3$): δ9.34(1H, s), 8.40 (1H, s), 8.33(1H, d, J=3.69 Hz), 7.75(1H, dt, J=2.02 Hz, 8.56 Hz), 7.65(1H, t, J=2.27 Hz), 7.59-7.44(3H, m), 7.39-7.14(1H, m), 7.20-7.03(3H, m), 6.98-6.88(2H, m), 6.76-6.67(2H, m), 4.87(2H, s), 4.52(1H, t, J=5.70 Hz), 4.42(2H, d, J=5.70 Hz).

Example 25

4-[3-chloro-4-(3-fluorobenzyloxy)-phenylamino]-6-(3-acetoxymethyl-phenyl)-quinazoline

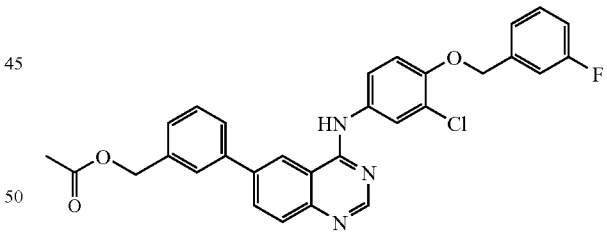

The 6-(3-acetoxymethyl-phenyl)-4-amino substituted quinazoline material (108 mg) was dissolved into of THF (10 mL), Et$_3$N (0.19 mL) and acetyl chloride (0.03 mL, 1.8 eq.) were added thereto sequentially in an ice-bath. The reaction was continued for 3 h, and the achieved product was purified to obtain the title compound. Yield: 72%.

¹H-NMR (400 MHz, CDCl$_3$): δ8.79(1H, s), 8.06-7.96(3H, m), 7.86(1H, d, J=2.69 Hz), 7.69-7.48(5H, m), 7.44-7.33(2H, m), 7.26-7.19(1H, m), 7.07-6.97(2H, m), 5.20(2H, s), 5.17 (2H, s), 2.13(3H, s).

Example 26

4-[3-chloro-4-(3-fluorobenzyloxy)-phenylamino]-6-[3-2-(methoxyethoxymethylene)-phenyl]-quinazoline

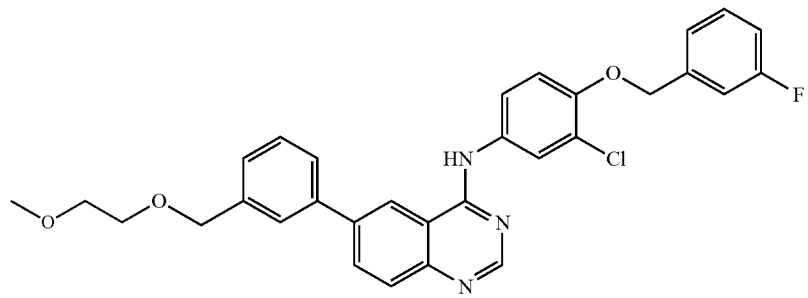

The 6-(3-acetoxymethyl-phenyl)-4-amino substituted quinazoline material (112 mg) was dissolved into DMF (10 ml), 2-methoxy-1-bromoethane (0.04 mL), Tetrabutylammonium iodide (10 mg) and Potassium carbonate (100 mg) were added thereto. The reaction was heated to 60° C. and continued for 8 h, and the title compound was obtained after post-treatment (64 mg, 51%).

$^1$H-NMR (400 MHz, CDCl$_3$): δ8.67(1H, d, J=2.2 Hz), 7.82(1H, dd, J=2.3 Hz, 8.7 Hz), 7.74-7.68(2H, m), 7.60(1H, d, J=7.69 Hz), 7.45(1H, t, J=7.69 Hz), 7.39-7.30(2H, m), 7.29-7.19(5H, m), 7.03-6.92(3H, m), 5.01(2H, s), 4.78(2H, s), 4.10(2H, t, J=4.95 Hz), 3.69(2H, t, J=4.95 Hz), 3.35(3H, s).

Example 27

4-[3-chloro-4-(3-fluorobenzyloxy)-phenylamino]-6-(5-hydroxymethyl-phenyl)-quinazoline ethyl-furan-2-yl)-quinazoline

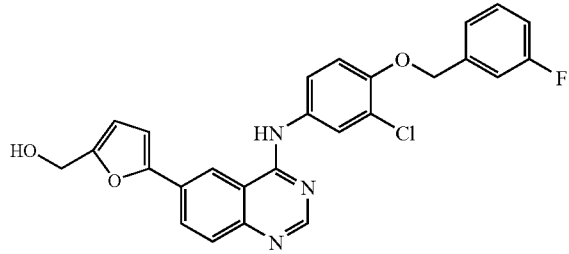

The 6-bromo-4-amino substituted quinazoline intermediate (3.00 g) and 5-formyl-2-furyl boronic acid (1.37 g) were dissolved into 1,4-dioxane (150 mL). Then Pd(PPh$_3$)4(1.50 g) and 20% aqueous Na$_2$CO$_3$ solution (7 mL) were added thereto under nitrogen atmosphere. The reaction was heated to 100° C. and continued for 2 h. The solvent was removed under reduced pressure, and the resulting residue was purified by column chromatography to obtain the 6-[2-(5-formylfuryl)]-4-amino substituted quinazoline intermediate.

The above intermediate was dissolved into a mixed solvent of THF/MeOH (2:1). NaBH$_4$ was added thereto at 0° C. in portions, and the reaction system turned dark gradually. After 30 min, most solvent was removed under reduced pressure, and the resulting residue was dissolved into ethyl acetate, washed with saturated saline, dried and purified by silica gel column chromatography to obtain the title compound (2.18 g, the total yield of the two steps is 70%).

$^1$H-NMR (400 MHz, CDCl$_3$): δ9.29(1H, s), 8.36(1H, s), 8.21(1H, d, J=8.38 Hz,), 7.73-7.68(1H, m), 7.60-7.58(1H, m), 7.45-7.35(2H, m), 7.04-6.96(1H, m), 6.92-6.82(2H, m), 6.70-6.60(2H, m), 6.50-6.47(1H, m), 6.08-6.02(1H, m), 4.80 (2H, d, J=6.04 Hz), 4.61(1H, t, J=5.63 Hz), 4.25(2H, t, J=6.87 Hz).

Example 28

4-[3-chloro-4-(3-fluorobenzyloxy)-phenylamino]-6-(5-methanesulfonyloxymethylene-furan-2-yl)-quinazoline

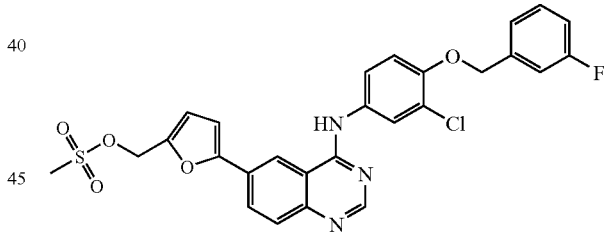

The above 6-[2-(5-hydroxymethyl-furyl)-4-amino substituted quinazoline material (250 mg) was dissolved into 25 mL of DMF. Et$_3$N (0.22 mL, 3.0 eq.) and methanesulfonyl chloride (0.06 mL, 1.5 eq.) were added thereto sequentially at room temperature while stirring. After the reaction was completed, the reaction mixture was diluted with large amount of ethyl acetate, washed with ice water and saturated aqueous ammonium chloride sequentially, and the organic phase was dried and concentrated. The resulting residue was purified by column chromatography to obtain the title compound (178 mg, 61%).

$^1$H-NMR (400 MHz, CDCl$_3$): δ8.66(1H, s), 8.19(1H, d, J=1.18 Hz), 8.03(1H, dd, J=1.57 Hz, 9.00 Hz), 7.91-7.87(1H, m), 7.62-7.55(2H, m), 7.40-7.33(1H, m), 7.28-7.20(3H, m), 7.06-7.68(2H, m), 6.77(1H, d, J=3.13 Hz), 6.49(1H, d, J=3.52 Hz), 5.17(2H, s), 4.51(2H, s), 3.44(3H, s).

Example 29

4-[3-chloro-4-(3-fluorobenzyloxy)-phenylamino]-6-(5-dimethylaminomethyl-furan-2-ylmethoxy)-quinazoline

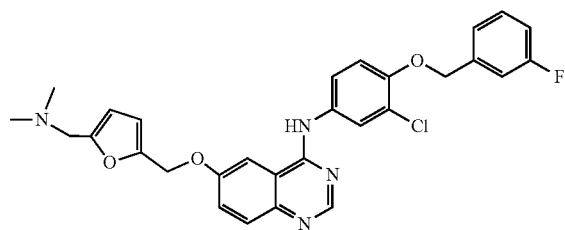

5-dimethylaminomethyl-furan-2-yl-methanol oil was obtained according to the method in the documents wherein dimethylamine, formaldehyde and furylmethanol were chosen as starting materials. 0.50 g of 5-dimethylaminomethyl-furan-2-yl-methanol was dissolved into 20 mL of $CH_2Cl_2$. Then $Et_3N$ and Methanesulfonyl chloride were added thereto sequentially. 5-dimethylaminomethyl-2-furanmethyl sulfonate was obtained after a post-treatment.

The above sulfonate (0.20 g) was dissolved into 20 mL of DMF. Then 6-hydroxy-4-amino substituted quinazoline material (0.20 g), tetrabutylammonium iodide (30 mg) and Potassium carbonate (105 mg) were added thereto. The mixture was heated to 50° C. and continued for 4 h. The title compound was obtained after post-treatment (129 mg, 48%).

$^1$H-NMR (400 MHz, $CDCl_3$): δ8.70(1H, s), 7.88-7.80(2H, m), 7.58-7.48(2H, m), 7.40-7.32(1H, m), 7.27-7.19(3H, m), 7.16(1H, d, J=2.44 Hz), 7.07-6.98(2H, m), 6.21-6.18(1H, m), 6.14-6.10(1H, m), 5.19(2H, s), 4.64(2H, s), 3.51(2H, s), 2.20(6H, s).

Example 30

4-[3-chloro-4-(3-fluorobenzyloxy)-phenylamino]-6-(3-(4-morph olino)propoxy)-7-methoxy-quinazoline

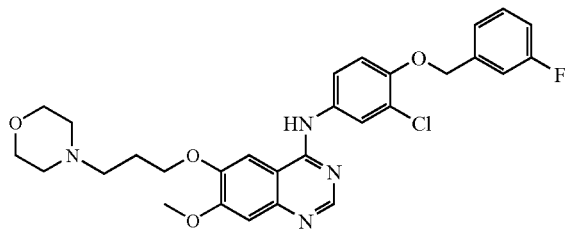

6,7-dimethoxy-quinazolone was reacted with methanesulfonic acid and L-methionine under reflux for 2 h, and then the mixture was poured into ice water to deposit a solid, which is 6-hydroxy-7-methoxy-quinazolone intermediate. After the hydroxyl group therein was protected by acylation, the intermediate was treated with $SOCl_2$ to obtain 4-chloro-6-acetoxy-7-methoxy-quinazoline.

The above moiety was reacted with 3-chloro-4-(3-fluorobenzyloxy)-aniline in isopropanol according to the related procedure as above to obtain 4-[3-chloro-4-(3-fluorobenzyloxy)-phenylamino]-6-acetoxy-7-methoxy-quinazoline; which was then treated with ammonia and the acetyl was hydrolyzed to obtain the intermediate 4-[3-chloro-4-(3-fluorobenzyloxy)-phenylamino]-6-hydroxy-7-methoxy-quinazoline.

The intermediate was reacted with excessive 3-(N-morpholino)-1-chloro-propane according to the procedure of Example 15 to obtain the title compound.

$^1$H-NMR (400 MHz, $CDCl_3$): δ9.46(1H, s), 8.45(1H, s), 7.95(1H, d, J=2.75 Hz), 7.80(1H, s), 7.59(1H, dd, J=2.44 Hz, 8.85 Hz), 7.52-7.44(1H, m), 7.39-7.26(3H, m), 7.23-7.15(2H, m), 5.25(2H, s), 4.17(2H, t, J=6.26 Hz), 3.93(3H, s), 3.59(4H, m), 2.49(2H, m), 2.39(41H, m), 2.00(2H, m).

Besides, the compound 30a in Table A is obtained in a similar method.

In the present invention, the anti-tumor experiment for the inventive compounds was conducted as below:

The inventive compounds were formulated into 5 concentrations. According to the improved MTT method of a live cell, 100 μl suspension with a concentration of $1.0×10^5$ A431 cells (human epidermoid squamous carcinoma cell) was inoculated into a 96-well plate, and then the test compounds solution were added individually until its final concentration; the mixture was incubated at 37° C. under humidity for 72 h, the plate was taken out and MTT was added to each well once again. The incubation was continued for another 6 h, and 100 μl SDS was added to end the reaction. The optical density (O.D.) of each well was assayed with an auto microplate reader, and the inhibitory rate was figured out, from which the concentration for 50% inhibition ($IC_{50}$) of each test compound could be calculated.

Wherein:
$IC_{50}$<1 μM was shown as "+++";
$IC_{50}$=1-10 μM was shown as "++";
$IC_{50}$=10-50 μM was shown as "+";
$IC_{50}$>50 μM was shown as "−". In the anti-tumor experiments for the compounds of the present invention, the calculated $IC_{50}$ was shown as follows:

| Example No. | $IC_{50}$ |
|---|---|
| 8 | +++ |
| 9 | ++ |
| 10 | + |
| 11 | ++ |
| 12 | +++ |
| 13 | ++ |
| 14 | ++ |
| 15 | ++ |
| 16 | ++ |
| 17 | +++ |
| 18 | + |
| 19 | ++ |
| 20 | +++ |
| 21 | ++ |
| 22 | + |
| 23 | + |
| 24 | ++ |
| 25 | +++ |
| 26 | ++ |
| 27 | ++ |
| 28 | ++ |
| 29 | ++ |
| 30 | ++ |

Example 31

Pharmaceutical Composition

The formulation was as follows:

| | |
|---|---|
| The compound obtained in Example 8 | 23 g |
| Starch | 140 g |
| microcrystallinecellulose | 67 g |

According to the general method, the above-mentioned materials were mixed uniformly, and then filled into general gelatin capsules to achieve 1000 capsules.

The capsules of the compound obtained in Example 9 could be prepared in similar method.

Example 32

1. Cell Line: A431 Human Epidermoid Squamous Carcinoma Cell

The procedure of Example 30 was repeated, and each of the test compound was formulated into five concentrations gradually. The 50% inhibitory concentration, $IC_{50}$ was determined. The result of the cell experiment was shown in Table A.

2. Cell Line: BT-474: Human Breast Cancer Cell

The cells were incubated with compounds of various concentrations (10-0.001 μm individually) for 5 days. The inhibition of cell proliferation was tested according to the SRB method, and the inhibitory rate was figure out. According to the inhibitory rate, the $IC_{50}$ was calculated by the Logit method. The anti-tumor activities in vitro were compared. The results of the cell experiment were shown in Table A

TABLE A

[Core structure: 4-anilinoquinazoline with substituents $R_1$, $R_1'$ on quinazoline 6,7-positions and $R_2$, $R_2'$ on aniline 4,3-positions]

| Compd. No. | R1 | R1' | R2 | R2' | A431 $IC_{50}$ | BT474 $IC_{50}$ |
|---|---|---|---|---|---|---|
| 8 | acrylamido (CH2=CH-C(O)-NH-) | H | 3-fluorobenzyloxy | Cl | 0.18, 0.11* | 0.001 |
| 9 | 4-methylphenylsulfonamido (Ts-NH-) | H | 3-fluorobenzyloxy | Cl | 1.22 | 0.28 |
| 10 | (E)-4-(dimethylamino)but-2-enamido | H | 3-fluorobenzyloxy | Cl | | |
| 11 | (E)-4-(dimethylamino)but-2-enamido | H | 3-fluorobenzyloxy | Cl | | |
| 12 | (E)-4-(dimethylamino)but-2-enamido | H | OCHF2 | Cl | | |
| 13 | (E)-4-(dimethylamino)but-2-enamido | H | OCH3 | Cl | | |
| 14 | acrylamido | H | OCH3 | Cl | 1.72 | 0.0069 |
| 15 | (E)-4-(dimethylamino)but-2-enamido | H | Cl | Cl | | |

TABLE A-continued

| Compd. No. | R1 | R1' | R2 | R2' | A431 IC$_{50}$ | BT474 IC$_{50}$ |
|---|---|---|---|---|---|---|
| 16 | acrylamide | Cl | 3-fluorobenzyloxy | Cl | | |
| 17 | acetoxy | Cl | 3-fluorobenzyloxy | H | 3.48 | 0.043 |
| 18 | HO- | H | 3-fluorobenzyloxy | Cl | | |
| 19 | 2-methoxyethoxy | H | 3-fluorobenzyloxy | Cl | 3.29, 1.70* | 0.088 |
| 20 | 3-morpholinopropoxy | H | 3-fluorobenzyloxy | Cl | 1.69 | 0.079 |
| 21 | methoxy | methoxy | 3-fluorobenzyloxy | Cl | 2.21 | 0.19 |
| 22 | Br | H | 3-fluorobenzyloxy | Cl | | |
| 23 | 4-methoxyphenyl | H | 3-fluorobenzyloxy | Cl | 23.97 | 0.17 |
| 24 | 3-(hydroxymethyl)phenyl | H | 3-fluorobenzyloxy | Cl | 3.87 | 0.086 |
| 25 | 3-(acetoxymethyl)phenyl | H | 3-fluorobenzyloxy | Cl | 2.38, 1.00* | 0.062 |

TABLE A-continued

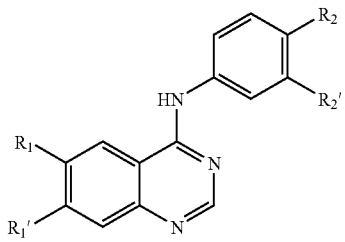

| Compd. No. | R1 | R1' | R2 | R2' | A431 IC$_{50}$ | BT474 IC$_{50}$ |
|---|---|---|---|---|---|---|
| 26 | methoxyethoxy-benzyl | H | 3-fluorobenzyloxy | Cl | 4.04 | 6.63 |
| 27 | hydroxymethyl-furan | H | 3-fluorobenzyloxy | Cl | 1.53, 1.03* | 0.023 |
| 28 | methylsulfonyloxymethyl-furan | H | 3-fluorobenzyloxy | Cl | 2.03 | 0.049 |
| 29 | dimethylaminomethyl-furan-methoxy | H | 3-fluorobenzyloxy | Cl | | |
| 30 | morpholinopropoxy | methoxy | 3-fluorobenzyloxy | Cl | 9.26 | 0.24 |
| 30a | methoxyethoxy | methoxy | 3-fluorobenzyloxy | Cl | 4.47 | 0.15 |

Note:
The compounds obtained in Example 8-30 are named as compd. 8-30 respectively.
*The two results from two experiments Example 33

The inhibitory effect of compound 8 and compound 14 on the phosphorylation activity of Erb-B2:

The concentration of the human breast cancer cells BT474 were adjusted to a suitable concentration, and inoculated into a plate. After treated with various compounds for 1.5 h, the cells were collected, cracked and the protein was adjusted to the same quantity. Following the protein-denaturation, SDS-PAGE was conducted, and transferred to nitric acid cellulose film; Hybriding with the anti-phosphorylation antibody (mono-anti), anti-β-tublin antibody (mono-anti) and anti-mouse-IgG antibody (bi-anti) respectively; Assayed by the ECL kit and the X-ray plate was exposed. According to the size and the density of the corresponding protein band, the inhibitory effect on Erb-B2 kinases can be evaluated.

The result was shown in FIG. 1: as compared with the market available drug Iressa, compound 8 and compound 14 have more superior inhibitory activity.

Example 34

The anti-tumor effect of compound 8 on human skin squamous cancer cell A431 grafted in a nude mouse:

A well-growth solid tumor of A431 was selected and incised into several pieces with the size of 2-3 mm; each was grafted into the right armpit of a mouse subcutaneously with a trocar respectively. After 7 days, the test compounds were administrated by gastric perfusion through the mouth for 13 days continuously. The long span (a) and the short span (b) of the tumor were measured with a vernier caliper every 4 days. According to the formula $V=ab^2/2$, the volume (mm$^3$) of the tumor could be calculated. The test animals were neck-off killed 23 days after the grafting. The test animals were anatomized to obtain the tumor. The tumors were weighed and the inhibitory rate was calculated.

The result was shown in the table below, which suggests that the inventive compounds have the significant inhibitory effect on the tumor.

| Group | Dosage (mg/kg) | Administration | Number of test animals start | Number of test animals end | Weight of the test animals (g) (tumor-off) | Weight of the inhibition tumor (g) $\bar{x} \pm SD$ | % |
|---|---|---|---|---|---|---|---|
| Control (corresponding solvent) | 25 ml/kg | ig × 13 | 7 | 7 | 22.40 ± 2.81 | 1.13 ± 0.18 | |
| Compound 8 | 25 | ig × 13 | 5 | 5 | 21.58 ± 2.18 | 0.79 ± 0.20** | 29.99 |
| | 50 | ig × 13 | 5 | 5 | 22.87 ± 3.96 | 0.69 ± 0.17** | 38.67 |
| | 100 | ig × 13 | 5 | 5 | 22.13 ± 1.83 | 0.64 ± 0.23** | 43.63 |

All documents referred to throughout this application are hereby incorporated in their entireties by reference, as if each of them has been individually incorporated. Further, it would be appreciated that, in light of the above described teaching of the invention, those skilled in the art could make various changes and modifications to the invention, and these equivalents would still fall within the scope of the invention as defined by the appended claims of the application.

The invention claimed is:

1. A compound of formula I, or a pharmaceutically acceptable salt, thereof,

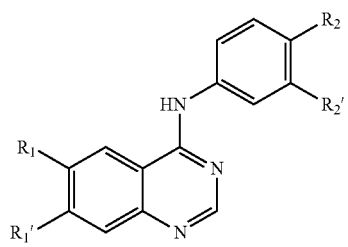

wherein
$R_1$ is acylamino of the formula:

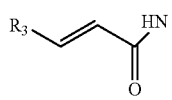

wherein $R_3$ is selected from hydrogen, N,N-dimethylaminomethyl, N,N-diethylaminomethyl, N,N-dipropylaminomethyl and N-morpholinomethyl;

$R_1'$ is selected from hydrogen, $C_1$-$C_4$ alkyl, $C_1$-$C_4$ alkyl substituted by halogens, $C_1$-$C_4$ alkoxy, or $C_1$-$C_4$ alkoxy substituted by halogens, and $R_2$ is selected from benzyloxy, mono-, di- and tri-halobenzyloxy; and $R_2'$ is halogen.

2. A compound of claim 1 or a pharmaceutically acceptable salt, thereof, wherein
$R_3$ is selected from hydrogen and N,N-dimethylaminomethyl.

3. The compound of claim 1, or a pharmaceutically acceptable salt, thereof, which is selected from the group consisting of:
N-{4-[3-chloro-4-(3-fluorobenzyloxy)-phenylamino]-quinazolin-6-yl}-acrylamide;
N-{4-[3-chloro-4-(3-fluorobenzyloxy)-phenylamino]-quinazolin-6-yl}-E, 4-(dimethylamino)-but-2-enamide;
N-[4-(3-chloro-4-benzyloxy-phenylamino)-quinazolin-6-yl]-E,4 (dimethylamino)-but-2-enamide;
N-{4-[3-chloro-4-(3-fluorobenzyloxy)-phenylamino]-7-trifluoro ethoxy-quinazolin-6-yl}-E,4-(dimethylamino)-but-2-enamide;
N-{4-[3-chloro-4-(3-fluorobenzyloxy)-phenylamino]-7-methoxy -quinazolin-6-yl}-E,4-(dimethylamino)-but-2-enamide;
N-{4-[3-chloro-4-(3-fluorobenzyloxy)-phenylamino]-7-methoxy-quinazolin-6-yl}-acrylamide.

4. A pharmaceutical composition, comprising 0.05-100mg of a compound of claim 1, or a pharmaceutically acceptable salt thereof, and a pharmaceutically acceptable carrier, excipient or diluent.

* * * * *